(12) United States Patent
Palmer et al.

(10) Patent No.: US 10,709,428 B2
(45) Date of Patent: Jul. 14, 2020

(54) NON-INVASIVE SKIN COLLECTION SYSTEM

(71) Applicant: DERMTECH, INC., La Jolla, CA (US)

(72) Inventors: Tara J. Palmer, San Diego, CA (US); John P. Alsobrook, II, Corrales, NM (US); John Dobak, La Jolla, CA (US)

(73) Assignee: DERMTECH, INC., La Jolla, CA (US)

( * ) Notice: Subject to any disclaimer, the term of this patent is extended or adjusted under 35 U.S.C. 154(b) by 415 days.

(21) Appl. No.: 15/571,247

(22) PCT Filed: Apr. 29, 2016

(86) PCT No.: PCT/US2016/030287
§ 371 (c)(1),
(2) Date: Nov. 1, 2017

(87) PCT Pub. No.: WO2016/179043
PCT Pub. Date: Nov. 10, 2016

(65) Prior Publication Data
US 2018/0110500 A1 Apr. 26, 2018

Related U.S. Application Data

(60) Provisional application No. 62/156,091, filed on May 1, 2015.

(51) Int. Cl.
*A61B 10/02* (2006.01)
*A61B 10/00* (2006.01)
(Continued)

(52) U.S. Cl.
CPC .............. *A61B 10/02* (2013.01); *A61B 10/00* (2013.01); *A61B 10/0096* (2013.01);
(Continued)

(58) Field of Classification Search
CPC ......... A61B 10/02; A61B 50/30; A61B 10/00; A61B 10/0096; A61B 2050/0065;
(Continued)

(56) References Cited

U.S. PATENT DOCUMENTS 4,122,947 A * 10/1978 Falla ...................... A61G 12/00
206/569
5,190,049 A * 3/1993 Briggs ............. A61B 5/150022
600/573
(Continued)

FOREIGN PATENT DOCUMENTS

WO WO-2010097773 A1 9/2010
WO WO-2016179043 A1 11/2016

OTHER PUBLICATIONS

Instructions for use DermTech adhesive skin biopsy kit. DermTech. Available at http://dermtech.com/wp-content/uploads/2015/10/dermtech-ifu-skin-collection-v7.pdf (Revised data Oct. 2015) (1 pg.).
(Continued)

*Primary Examiner* — Navin Natnithithadha
(74) *Attorney, Agent, or Firm* — Wilson Sonsini Goodrich & Rosati

(57) ABSTRACT

The subject matter described herein provides non-invasive tape stripping methods for the collection of a skin sample. The tape stripping method includes applying and removing at least one adhesive tape, provided that a skin sample is adhered to the adhesive tape after removal. The at least one adhesive tape is supplied in an adhesive skin sample collection kit. The adhesive skin sample collection kit further comprises a sample collector and instructions for use sheet.

30 Claims, 3 Drawing Sheets

(51) Int. Cl.
*A61B 50/30* (2016.01)
*A61B 17/00* (2006.01)
*A61B 50/00* (2016.01)

(52) U.S. Cl.
CPC ...... *A61B 50/30* (2016.02); *A61B 2010/0225* (2013.01); *A61B 2017/00761* (2013.01); *A61B 2017/00774* (2013.01); *A61B 2017/00951* (2013.01); *A61B 2050/0065* (2016.02); *A61B 2050/3015* (2016.02)

(58) Field of Classification Search
CPC .... A61B 2050/3015; A61B 2010/0225; A61B 2017/00761; A61B 2017/00774; A61B 2017/00951
USPC ........................................................ 600/572
See application file for complete search history.

(56) References Cited

U.S. PATENT DOCUMENTS

| | | | | |
|---|---|---|---|---|
| 5,921,396 A | * | 7/1999 | Brown, Jr. ........... | A61B 10/007 206/223 |
| 6,106,732 A | * | 8/2000 | Johnston ............... | B01L 3/5023 210/503 |
| 6,176,836 B1 | * | 1/2001 | Trudil ................. | A61B 10/0096 206/363 |
| 6,447,463 B1 | * | 9/2002 | Borkowski ........ | A61B 10/0035 600/562 |
| 7,921,999 B1 | * | 4/2011 | Kimball ............ | A61F 13/00063 206/440 |
| 2003/0045810 A1 | * | 3/2003 | Borkowski ........ | A61B 10/0035 600/562 |
| 2007/0087323 A1 | * | 4/2007 | Armitage ............... | B65D 65/46 435/2 |
| 2007/0243537 A1 | * | 10/2007 | Tuck ...................... | G06Q 50/22 435/6.16 |
| 2010/0105102 A1 | * | 4/2010 | Hanes .................... | A61B 10/02 435/29 |

OTHER PUBLICATIONS

PCT/US2016/30287 International Preliminary Report on Patentability dated Nov. 16, 2017.
PCT/US2016/30287 International Search Report and Written Opinion dated Aug. 16, 2016.

* cited by examiner

NON-INVASIVE SKIN COLLECTION SYSTEM

CROSS REFERENCE

This application is a U.S. National Phase of International Application No. PCT/US2016/030287, filed Apr. 29, 2016, which claims the benefit of U.S. Provisional Application No. 62/156,091, filed May 1, 2015, which is incorporated herein by reference in its entirety.

BACKGROUND OF THE INVENTION

Skin diseases are some of the most common human illnesses and represent an important global burden in healthcare. Three skin diseases are in the top ten most prevalent diseases worldwide, and eight fall into the top 50. When considered collectively, skin conditions range from being the second to the 11th leading causes of years lived with disability.

SUMMARY OF THE INVENTION

Skin diseases include eczema, psoriasis, acne vulgaris, pruritus, alopecia areata, decubitus ulcer, urticaria, scabies, fungal skin diseases, impetigo, abscess, bacterial skin diseases, cellulitis, lupus, viral warts, molluscum contagiosum and cancers, such as melanomas. Indeed, the deadliest skin cancer is melanoma. Melanoma is currently the fastest growing cancer with the incidence rate of melanoma having doubled since 1973. While there has been a 20% decline in cancer deaths overall since 1991, melanoma is one of three cancers facing increasing rates of death. Because approximately 62% of melanomas and 45% of melanoma deaths occur prior to age 65, melanoma places significant burdens on the healthcare system. If diagnosed and removed early in its evolution, when confined to the outermost skin layer and deemed to be non-invasive or "in situ" (Stage 0), patients have an expected survival rate of almost 100%. Invasive melanomas that are thin and extend into the uppermost regions of the second skin layer still have cure rates greater than 90%. However, once the cancer advances into the deeper layers of skin, the risk of metastasis increases.

The inventors of the present disclosure have identified a need for improvement of skin disease prevention, diagnosis and treatment to improve patient well-being and alleviate burdens on global health efforts. As described herein, pigmented skin lesions suspicious for melanoma can be assessed for diagnosis by both visual observation and biopsy. Current tools commonly used to aid the biopsy decision have modest sensitivity and low specificity and include clinical grading criteria (eg., ABCDE attributes) and lesion magnification with a dermatoscope. Visible observation and pathologic assessment of these lesions is challenging, making melanoma one of the top five misdiagnosed cancers. Similar to visual evaluation of pigmented lesions, histopathologic assessment of pigmented lesions is also subjective and challenging. Because patients can have many atypical lesions, the decision of which lesions to biopsy can be challenging and it is not practical to biopsy all lesions. Pigmented lesions with a lower suspicion for melanoma, and likely earlier stages, may not be selected for biopsy such that 10%-30% may have a delayed diagnosis. Of the millions of surgical biopsies performed each year on selected pigmented skin lesions, over 95% are negative for melanoma and represent an unnecessary surgical procedure.

Lesions positive for melanoma are subsequently staged to determine if the tumor remains in situ or if it has undergone invasion. For early melanoma, this staging can be difficult and is also dependent on the area selected for examination. It is important to identify the stage accurately, because invasive melanoma has a lower survival rate, requires more extensive medical treatment, surveillance, work up and has a higher cost. The medical work up for invasive melanoma may include a sentinel lymph node biopsy surgical procedure to determine if the melanoma has metastasized. This is a significant surgical procedure with associated high cost and morbidity with results that can be ambiguous.

Provided herein are methods and systems for non-invasive skin sampling using an adhesive tape. According to one feature of the subject matter described herein, an adhesive tape having a first central collection area and a second area extending from the periphery of the first collection area is provided. The first central collection area of the adhesive tapes has a skin facing surface comprising an adhesive matrix. In some embodiments, the first central collection area of the adhesive tape has a second surface opposite the surface comprising the adhesive matrix. The second area of the adhesive tape is useful as a tab, to apply and remove the adhesive tape from a skin surface. The adhesive tape is configured for application to a skin surface so that an effective amount of a skin sample adheres to the adhesive matrix. In some embodiments, the effective amount of the skin sample comprises no more than about 1 microgram of cellular material. In some embodiments, the effective amount of the skin sample comprises from about 50 microgram to about 1 gram of cellular material. In some embodiments, the effective amount of the skin sample comprises between about 50 microgram to about 500 microgram, between about 100 microgram to about 450 microgram, between about 100 microgram to about 350 microgram, between about 100 microgram to about 300 microgram, between about 120 microgram to about 250 microgram, or between about 150 microgram to about 200 microgram of cellular material. In some embodiments, an effective amount of a skin sample is an amount sufficient to isolate and identify the cellular material. In some embodiments, the adhered skin sample comprises a cellular material that removably adheres to the adhesive tape. In some embodiments, the cellular material is a nucleic acid such as RNA or DNA. In some embodiments, the effective amount of the skin sample comprises between about 50 microgram to about 500 microgram, between about 100 microgram to about 450 microgram, between about 100 microgram to about 350 microgram, between about 100 microgram to about 300 microgram, between about 120 microgram to about 250 microgram, or between about 150 microgram to about 200 microgram of RNA material. In some embodiments, the cellular material is no more than about 1 nanogram of RNA material.

In some embodiments, the adhesive tape does not contain latex, silicone, or does not contain either of these agents. In some embodiments, the matrix of the adhesive tape is comprised of a synthetic rubber compound. In some embodiments, the first collection area of the adhesive tape is comprised of a transparent material. In some embodiments, the second area of the adhesive tape is comprised of a transparent material. In some embodiments, the adhesive tape is comprised of a flexible material. In some embodiments, the first central collection area and the second area are comprised of different materials. In some embodiments, the first central collection area of the adhesive tape is comprised of a polyurethane carrier film. In some embodiments, the first central collection area of the adhesive tape has an elliptical shape. In some embodiments, the longest length of the first central collection area is from about 5 mm to about 50 mm.

According to one feature of the subject matter described herein, an adhesive tape is provided on a tri-fold skin sample collector configured to hold the adhesive tape. The adhesive tape has a first central collection area and a second area extending from the periphery of the first collection area is provided. The first central collection area of the adhesive tapes has a skin facing surface comprising an adhesive matrix. In some embodiments, the first central collection area of the adhesive tape has a second surface opposite the surface comprising the adhesive matrix. The second area of the adhesive tape is useful as a tab, for applying and removing the adhesive tape from a skin surface. The adhesive tape is configured for application to a skin surface so that an effective amount of a skin sample adheres to the adhesive matrix. In some embodiments, the effective amount of the skin sample comprises no more than about 1 microgram of cellular material. In some embodiments, an effective amount of a skin sample is an amount sufficient to isolate and identify the cellular material. In some embodiments, the effective amount of the skin sample comprises from about 50 microgram to about 1 gram of cellular material. In some embodiments, the effective amount of the skin sample comprises between about 50 microgram to about 500 microgram, between about 100 microgram to about 450 microgram, between about 100 microgram to about 350 microgram, between about 100 microgram to about 300 microgram, between about 120 microgram to about 250 microgram, or between about 150 microgram to about 200 microgram of cellular material. In some embodiments, the adhered skin sample comprises a cellular material that removably adheres to the adhesive tape.

In some embodiments, the tri-fold skin sample collector comprises three panels. The tri-fold skin sample collector includes a peelable release panel and a placement area panel. In some embodiments, one panel of the tri-fold skin sample collector is a clear panel. In some embodiments, the tri-fold skin sample collector is labeled with a unique barcode that is assigned to a patient sample. In some embodiments, the placement area panel of the tri-fold skin sample collector comprises a removable liner. In some embodiments, the adhesive tape is affixed to the peelable release panel prior to skin application. In some embodiments, the peelable release panel of the tri-fold skin sample collector is configured to hold between about 1 to about 12 adhesive tapes, between about 2 to about 12 adhesive tapes, 1 to about 8 adhesive tapes, between 4 to 10 adhesive tapes, between 6 to 10 adhesive tapes, between 6 to 8 adhesive tapes, or between 4 to 8 adhesive tapes provided that the adhesive tapes have not been applied to a skin surface. In some embodiments, the peelable release panel is configured to hold 8 adhesive tapes, provided that the adhesive tapes have not been applied to a skin surface. In some embodiments, the peelable release panel is configured to hold 4 adhesive tapes, provided that the adhesive tapes have not been applied to a skin surface. In some embodiments, the adhesive tape is affixed to the placement panel after skin application, provided that the adhesive tape comprises an effective amount of a skin sample. In some embodiments, the placement area panel of the tri-fold skin sample collector is configured to hold between about 1 to about 12 adhesive tapes, between about 2 to about 12 adhesive tapes, 1 to about 8 adhesive tapes, between 4 to 10 adhesive tapes, between 6 to 10 adhesive tapes, between 6 to 8 adhesive tapes, or between 4 to 8 adhesive tapes provided that each adhesive tape comprises an effective amount of a skin sample. In some embodiments, the placement area panel of the tri-fold skin sample collector is configured to hold 8 adhesive tapes, provided that each adhesive tape comprises an effective amount of a skin sample. In some embodiments, the placement area panel of the tri-fold skin sample collector is configured to hold 4 adhesive tapes, provided that each adhesive tape comprises an effective amount of a skin sample.

According to one aspect of the subject matter, a non-invasive method for isolating a skin sample is provided. The skin sample is isolated by applying an adhesive tape to a desired skin surface, where the skin sample adheres to the adhesive matrix, and removing the adhesive tape, stripping an adhered skin sample from the skin surface. In some embodiments, the adhesive tape is slowly removed from the skin in one direction. In some embodiments, the person applying the adhesive tape wears gloves. The adhesive tape has a first central collection area and a second area extending from the periphery of the first collection area is provided. The first central collection area of the adhesive tapes has a skin facing surface comprising an adhesive matrix. In some embodiments, the first central collection area of the adhesive tape has a second surface opposite the surface comprising the adhesive matrix. The second area of the adhesive tape is useful as a tab, for applying and removing the adhesive tape from a skin surface. The adhesive tape is configured for application to a skin surface so that an effective amount of a skin sample adheres to the adhesive matrix. In some embodiments, the effective amount of the skin sample comprises no more than about 1 microgram of cellular material. In some embodiments, an effective amount of a skin sample is an amount sufficient to isolate and identify the cellular material. In some embodiments, the adhered skin sample comprises a cellular material that removably adheres to the adhesive tape.

In some embodiments, the adhesive matrix of the adhesive tape is comprised of a synthetic rubber compound. In some embodiments, the adhesive tape is comprised of a transparent material. In some embodiments, the adhesive tape is comprised of a flexible material.

In some embodiments, prior to applying the adhesive tape to a desired skin surface, the skin facing surface of the first central collection area does not come in contact with a skin surface other than the desired skin surface to be sampled. In some embodiments, prior to applying the adhesive tape to a desired skin surface, the adhesive matrix of the first central collection area does not come in contact with a skin surface other than the desired skin surface to be sampled.

In some embodiments, the skin surface is prepared for skin sampling by removing any hairs on the skin surface, cleansing the surface with an antiseptic, drying the surface completely prior to application of the adhesive tape, or any combination thereof. In some embodiments, the antiseptic comprises an alcohol. In some embodiments, the alcohol is isopropyl alcohol.

In some embodiments, the method includes first removing the adhesive tape from a peelable release panel of a tri-fold skin sample collector prior to applying the adhesive tape to the desired skin surface to be sampled. In some embodiments, the tri-fold skin sample collector includes three panels. In some embodiments, the tri-fold skin sample collector includes a peelable release panel. In some embodiments, the tri-fold skin sample collector includes a placement area panel. In some embodiments, the tri-fold skin sample collector includes a clear panel. In some embodiments, the tri-fold skin sample collector is labeled with a unique barcode that is assigned to a patient skin sample. In some embodiments, the method includes filling out patient information on the tri-fold skin sample collector. In some embodiments, the method includes placing the adhesive tape and the adhered skin sample onto a placement area panel of the tri-fold skin sample collector, provided that the adhesive matrix side of the tape is facing toward the placement area panel. In some embodiments, the method includes removing a removable liner from the placement area panel of the tri-fold skin sample collector prior to placing the adhesive tape onto the placement area panel.

In some embodiments, the method comprises applying and removing between about 1 to about 12 adhesive tapes, between about 2 to about 12 adhesive tapes, 1 to about 8 adhesive tapes, between 4 to 10 adhesive tapes, between 6 to 10 adhesive tapes, between 6 to 8 adhesive tapes, or between 4 to 8 adhesive tapes sequentially to and from the skin surface. In some embodiments, the method comprises applying and removing 8 adhesive tapes sequentially to and from the skin surface. In some embodiments, the method comprises applying and removing 4 adhesive tapes sequentially to and from the skin surface.

In some embodiments, the method includes holding the skin surface taut and pressing the adhesive tape firmly on the skin surface while making circular motions on the adhesive tape prior to removing the adhesive tape from the skin surface. In some embodiments, 1-20 circular motions are made on the adhesive tape. In some embodiments, 15 circular motions are made on the adhesive tape.

In some embodiments, the adhesive tape is applied onto a skin lesion of the skin surface. In some embodiments, the skin lesion is a pigmented skin lesion comprising a mole, dark colored skin spot, or melanin containing skin area. In some embodiments, the skin lesion is suspicious for skin diseases including, but not limited to, melanoma, lupus, rubeola, acne, hemangioma, psoriasis, eczema, candidiasis, impetigo, shingles, leprosy, Chron's disease, inflammatory dermatoses, bullous diseases, infections, basal cell carcinoma, actinic keratoses, merkel cell carcinoma, sebaceous carcinoma, squamous cell carcinoma, and dermatofibrosarcoma protuberans. In some embodiments, the skin lesion is from about 5 mm to about 20 mm in diameter.

In some embodiments, the adhesive tape is applied on a skin surface that is not located on the areas including, but limited to, palms, soles of feet, and mucous membranes. In some embodiments, the adhesive tape is applied to a skin surface located on the areas including, but not limited to, the face, neck, arm, chest, abdomen, back, or legs. In some embodiments, the skin surface is not ulcerated or bleeding. In some embodiments, the skin surface has not been previously biopsied.

In some embodiments, the method further comprises applying the adhesive tape to a skin lesion on the skin surface and demarcating on the adhesive tape a zone around the skin lesion on a second surface of the adhesive tape. The second surface of the adhesive tape is the surface which is not the skin facing surface and does not comprise the adhesive matrix. In some embodiments, a permanent marker is used to demarcate the skin lesion zone.

In some embodiments, the method further comprises detecting the presence of a nucleic acid molecule expressed from C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some embodiments, the method comprises detecting the presence of a nucleic acid molecule expressed from Table 1 in the skin sample. In some embodiments, the method comprises detecting the presence of a nucleic acid molecule expressed from C6orf218 or PRAME in the skin sample. In some embodiments, the method comprises detecting the presence of a nucleic acid molecule expressed from C6orf218 in the skin sample.

According to one aspect of the subject matter, a system for collecting and mailing a skin sample from a patient is provided. The system includes, but is not limited to, at least one adhesive tape, an instructions for use sheet (or instruction manual), and a sample collector. The adhesive tape has a first central collection area and a second area extending from the periphery of the first collection area is provided. The first central collection area of the adhesive tapes has a skin facing surface comprising an adhesive matrix. In some embodiments, the first central collection area of the adhesive tape has a second surface opposite the surface comprising the adhesive matrix. The second area of the adhesive tape is useful as a tab, for applying and removing the adhesive tape from a skin surface. The adhesive tape is configured for application to a skin surface so that an effective amount of a skin sample adheres to the adhesive matrix. In some embodiments, the effective amount of the skin sample comprises no more than about 1 microgram of cellular material. In some embodiments, the effective amount of the skin sample comprises between about 50 microgram to about 500 microgram, between about 100 microgram to about 450 microgram, between about 100 microgram to about 350 microgram, between about 100 microgram to about 300 microgram, between about 120 microgram to about 250 microgram, or between about 150 microgram to about 200 microgram of cellular material. In some embodiments, an effective amount of a skin sample is an amount sufficient to isolate and identify the cellular material. In some embodiments, the adhered skin sample comprises a cellular material that removably adheres to the adhesive tape. The instructions for use sheet instructs for the non-invasive removal of a skin sample including application of the adhesive tape to the skin, and removal of the adhesive tape from the skin.

In some embodiments, the sample collector is a tri-fold skin sample collector. In some embodiments, the sample collector is labeled with a unique barcode that is assigned to the patient skin sample. In some embodiments, the sample collector comprises an area for labeling patient information. In some embodiments, the sample collector includes a peelable release panel. In some embodiments, the sample collector includes a placement area panel. In some embodiments, the sample collector includes a clear panel. In some embodiments, at least one adhesive tape is affixed to a peelable release panel of the sample collector. In some embodiments, between about 1 to about 12 adhesive tapes, between about 2 to about 12 adhesive tapes, 1 to about 8 adhesive tapes, between 4 to 10 adhesive tapes, between 6 to 10 adhesive tapes, between 6 to 8 adhesive tapes, or between 4 to 8 adhesive tapes adhesive tapes are affixed to a peelable release panel of the sample collector.

In some embodiments, the system includes a lab requisition form. In some embodiments, the lab requisition form is labeled with a unique barcode that is assigned to the patient sample. In some embodiments, the system includes a permanent marker. In some embodiments, the system includes a resealable plastic bag. In some embodiments, the system includes a package for shipping. In some embodiments, the package for shipping includes a prepaid shipping label.

BRIEF DESCRIPTION OF THE DRAWINGS

The novel and inventive features of the subject matter described herein are set forth with particularity in the appended claims. A better understanding of the feature and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
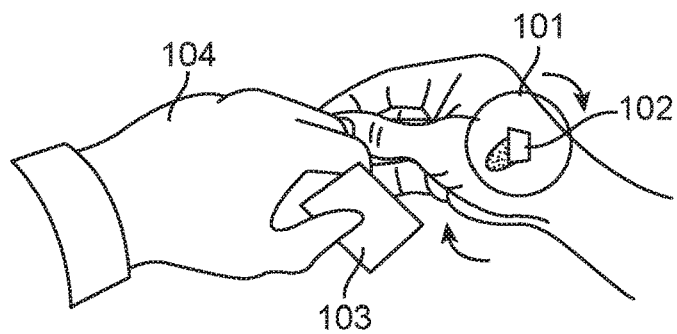
FIG. 1 is illustrative of cleansing a skin sampling area comprising a skin lesion.

The subject matter described herein is based on a non-invasive tape stripping method for the collection of a skin sample. The tape stripping method is performed using an adhesive skin sample collection kit. The tape stripping method involves applying and removing an adhesive tape to the skin surface of a subject. The adhesive tape comprises an adhesive matrix, wherein during application of the adhesive tape to the skin surface, an effective amount of a skin sample containing cellular material adheres to the adhesive matrix. The adhered skin sample is retained on the adhesive matrix upon removal of the tape from the skin surface. The adhesive tape containing the adhered skin sample is designated as a used adhesive tape. The adhesive tape is configured so that at least a portion of the skin sample cellular material can be harvested from a used tape.

Non-Invasive Tape Striping and Analysis

The adhesive skin sample collection kit for use with tape stripping methods is provided as a non-invasive means to collect skin samples with minimal discomfort. Cellular material is isolated from the skin sample and can be utilized in tests that can determine the stage of disease, the risk of disease progression and a patient's likelihood of responding to a particular treatment. Treatments include drug therapies and biopsy. Skin sample cellular materials include nucleic acids, polypeptides, lipids, carbohydrates and small molecules. Nucleic acids include DNA and RNA.

In some embodiments, isolated RNA from a collected skin sample is reverse transcribed into cDNA for amplification by PCR to enrich for target genes. The expression levels of these target genes are quantified by quantitative PCR in a gene expression test. A gene expression test provides information on a gene expression signature associated with a disease. A pigmented lesion assay is an exemplary gene expression test which measures the expression levels of target genes from RNA isolated using the adhesive skin sample collection kit.

For example, in some embodiments, the pigmented lesion assay provides objective information on a gene expression signature associated with melanoma. This information can be used to help support a histopathologic diagnosis or to determine the need for a biopsy, thereby reducing unnecessary biopsy procedures. The development of invasive tumor properties is also controlled by gene expression; therefore the pigmented lesion assay may also differentiate invasive melanoma from melanoma in situ as well as provide staging information. The identification of invasive melanoma with metastatic potential will direct treatments to only those who need it. Another gene expression assay may determine if a melanoma tumor has spread to the lymph nodes. This test can reduce the need for a sentinel lymph node surgery, which can be extensive, cause morbidity and has significant medical costs.

Gene expression analyses facilitate drug development by identifying drug targets and stratifying patients into groups that will maximize a drug response. In an exemplary embodiment, a skin sample collected from the face of a subject with lupus is isolated and utilized in a gene expression test to assess the expression of target genes indicated in lupus drug effects. This gene expression test can identify responders to therapy and identify new drug targets. The use of the adhesive tape allows for skin sample collection without the scarring that can occur with a biopsy.

In some embodiments, one or more polypeptides isolated from the used adhesive tape are detected and/or quantified. For example, in some embodiments, one or more polypeptides isolated from the used adhesive tape are detected and/or quantified using ELISA, immunohistochemistry, mass spectrometry, and/or absorbance measurement. In some embodiments, the sequence of DNA isolated from the used adhesive tape is determined using gene sequencing methods known to one of skill in the art.

In some instances, the skin sample collected using the tape stripping method is used in combination with other clinical assays including immunohistochemistry, immunophenotyping, fluorescent in situ hybridization (FISH), and/or any combination thereof. The skin sample does not necessarily need to be removed from the adhesive tape to prove useful as an assay component. Cellular material from the skin samples can be detected from the surface of the adhesive tape matrix. Detection methods include the use of probes configured to bind to cellular material adhered to the adhesive tape matrix. Probes include, but are not limited to, primers configured to bind to nucleic acids, and antibodies configured to bind to polypeptides, nucleic acids, small molecules, lipids, and/or carbohydrates.

In some embodiments, the tape stripping method is part of the work up for a variety of suspected skin conditions including, but not limited to, lupus, rubeola, acne, hemangioma, psoriasis, eczema, candidiasis, impetigo, shingles, leprosy and Chron's disease. Skin conditions also include inflammatory dermatoses, bullous diseases, infections and cancers. Skin cancers include, but are not limited to, basal cell carcinoma, actinic keratoses, merkel cell carcinoma, sebaceous carcinoma, squamous cell carcinoma, melanoma and dermatofibrosarcoma protuberans.

In some embodiments, the tape stripping method is performed using a plurality of adhesive tapes. Between 1 and 8 adhesive tapes can be sequentially applied and removed to collect a skin sample. The number of adhesive tapes used per skin sample may include, but is not limited to, 12, 11, 10, 9, 8, 7, 6, 5, 4, 3, 2, 1, from about 2 to about 7, from about 3 to about 6, and from about 4 to about 5. In certain instances, an adhesive tape is applied to the skin and removed from the skin about 1 to about 8 times.

Components of the Collection Kit

The adhesive tape of the adhesive skin sample collection kit typically comprises a first collection area comprising an adhesive matrix and a second area extending from the periphery of the first collection area. The adhesive matrix is located on a skin facing surface of the first collection area. The second area functions as a tab, suitable for applying and removing the adhesive tape. The tab is sufficient in size so that while applying the adhesive tape to a skin surface, the applicant does not come in contact with the matrix material of the first collection area. In some embodiments, the adhesive tape does not contain a second area tab. In some instances, the adhesive tape is handled with gloves to reduce contamination of the adhesive matrix prior to use.

In some embodiments, the first collection area is a polyurethane carrier film. In some embodiments, the adhesive matrix is comprised of a synthetic rubber compound. In some embodiments, the adhesive matrix is a styrene-isoprene-styrene (SIS) linear block copolymer compound. In some instances, the adhesive tape does not comprise latex, silicone, or both. In some instances, the adhesive tape is manufactured by applying an adhesive material as a liquid-solvent mixture to the first collection area and subsequently removing the solvent.

The matrix material is sufficiently sticky to adhere to a skin sample. The matrix material is not so sticky that is causes scarring or bleeding or is difficult to remove. In some embodiments, the matrix material is comprised of a transparent material. In some instances, the matrix material is biocompatible. In some instances, the matrix material does not leave residue on the surface of the skin after removal. In certain instances, the matrix material is not a skin irritant.

In some embodiments, the adhesive tape comprises a flexible material, enabling the tape to conform to the shape of the skin surface upon application. In some instances, at least the first collection area is flexible. In some instances, the tab is plastic. In an illustrative example, the adhesive tape does not contain latex, silicone, or both. In some embodiments, the adhesive tape is made of a transparent material, so that the skin sampling area of the subject is visible after application of the adhesive tape to the skin surface. The transparency ensures that the adhesive tape is applied on the desired area of skin comprising the skin area to be sampled. In some embodiments, the adhesive tape is between about 5 and about 100 mm in length. In some embodiments, the first collection area is between about 5 and about 40 mm in length. In some embodiments, the first collection area is between about 10 and about 20 mm in length. In some embodiments the length of the first collection area is configured to accommodate the area of the skin surface to be sampled, including, but not limited to, about 19 mm, about 20 mm, about 21 mm, about 22 mm, about 23 mm, about 24 mm, about 25 mm, about 30 mm, about 35 mm, about 40 mm, about 45 mm, about 50 mm, about 55 mm, about 60 mm, about 65 mm, about 70 mm, about 75 mm, about 80 mm, about 85 mm, about 90 mm, and about 100 mm. In some embodiments, the first collection area is elliptical.

In further embodiments, the adhesive tape of this invention is provided on a peelable release sheet in the adhesive skin sample collection kit. In some embodiments, the adhesive tape provided on the peelable release sheet is configured to be stable at temperatures between −80® C. and 30® C. for at least 6 months, at least 1 year, at least 2 years, at least 3 years, and at least 4 years. In some instances, the peelable release sheet is a panel of a tri-fold skin sample collector.

The peelable release sheet is configured to hold a plurality of adhesive tapes, including, but not limited to, 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. The peelable release sheet is configured to hold about 12 adhesive tapes. The peelable release sheet is configured to hold about 11 adhesive tapes. The peelable release sheet is configured to hold about 10 adhesive tapes. The peelable release sheet is configured to hold about 9 adhesive tapes. The peelable release sheet is configured to hold about 8 adhesive tapes. The peelable release sheet is configured to hold about 7 adhesive tapes. The peelable release sheet is configured to hold about 6 adhesive tapes. The peelable release sheet is configured to hold about 5 adhesive tapes. The peelable release sheet is configured to hold about 4 adhesive tapes. The peelable release sheet is configured to hold about 3 adhesive tapes. The peelable release sheet is configured to hold about 2 adhesive tapes. The peelable release sheet is configured to hold about 1 adhesive tape.

The adhesive tape is applied to the skin and removed from the skin. After removing the used adhesive tape from the skin surface, the tape stripping method further comprises storing the used tape on a placement area sheet, where the tape remains until the skin sample is isolated or otherwise utilized. The used tape is configured to be stored on the placement area sheet for at least 1 week at temperatures between −80® C. and 30® C. In some embodiments, the used tape is configured to be stored on the placement area sheet for at least 2 weeks, at least 3 weeks, at least 1 month, at least 2 months, at least 3 months, at least 4 months, at least 5 months, and at least 6 months at temperatures between −80® C. to 30® C.

In some instances, the placement area sheet comprises a removable liner, provided that prior to storing the used tape on the placement area sheet, the removable liner is removed. The placement area sheet is configured to hold a plurality of adhesive tapes, including, but not limited to, 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. The placement area sheet is configured to hold about 12 adhesive tapes. The placement area sheet is configured to hold about 11 adhesive tapes. The placement area sheet is configured to hold about 10 adhesive tapes. The placement area sheet is configured to hold about 9 adhesive tapes. The placement area sheet is configured to hold about 8 adhesive tapes. The placement area sheet is configured to hold about 7 adhesive tapes. The placement area sheet is configured to hold about 6 adhesive tapes. The placement area sheet is configured to hold about 5 adhesive tapes. The placement area sheet is configured to hold about 4 adhesive tapes. The placement area sheet is configured to hold about 3 adhesive tapes. The placement area sheet is configured to hold about 2 adhesive tapes. The placement area sheet is configured to hold about 1 adhesive tape.

The used tape is stored so that the matrix containing, skin facing surface of the used tape is in contact with the placement area sheet. In some instances, the placement area sheet is a panel of the tri-fold skin sample collector. In some instances, the tri-fold skin sample collector may further comprise a clear panel. The tri-fold skin sample collector may be labeled with a unique barcode that is assigned to a subject. In some instances, the tri-fold skin sample collector comprises an area for labeling subject information.

In an illustrative embodiment, the adhesive skin sample collection kit comprises the tri-fold skin sample collector comprising adhesive tapes stored on a peelable release panel. In some instances, the tri-fold skin sample collector further comprises a placement area panel with a removable liner. The tape stripping method involves removing an adhesive tape from the tri-fold skin sample collector peelable release panel, applying the adhesive tape to a skin sample, removing the used adhesive tape containing a skin sample and placing the used tape on the placement area sheet. In some instances the placement area panel is a single placement area panel sheet. The identity of the skin sample collected is indexed to the tri-fold skin sample collector or placement area panel sheet by using a barcode or printing patient information on the collector or panel sheet. The indexed tri-fold skin sample collector or placement sheet is sent to a diagnostic lab for processing. The used tape is configured to be stored on the placement panel for at least 1 week at temperatures between −80® C. and 25® C. In some embodiments, the used tape is configured to be stored on the placement area panel for at least 2 weeks, at least 3 weeks, at least 1 month, at least 2 months, at least 3 months, at least 4 months, at least 5 months, and at least 6 months at temperatures between −80® C. and 25® C. In some embodiments the indexed tri-fold skin sample collector or placement sheet is sent to a diagnostic lab using UPS or FedEx.

In an exemplary embodiment, the tape stripping method further comprises preparing the skin sample prior to application of the adhesive tape. Preparation of the skin sample includes, but is not limited to, removing hairs on the skin surface, cleansing the skin surface and/or drying the skin surface. In some instances, the skin surface is cleansed with an antiseptic including, but not limited to, alcohols, quaternary ammonium compounds, peroxides, chlorhexidine, halogenated phenol derivatives and quinolone derivatives. In some instances, the alcohol is about 0 to about 20%, about 20 to about 40%, about 40 to about 60%, about 60 to about 80%, or about 80 to about 100% isopropyl alcohol. In some instances, the antiseptic is 70% isopropyl alcohol.

In some embodiments, the tape stripping method is used to collect a skin sample from the surfaces including, but not limited to, the face, head, neck, arm, chest, abdomen, back, leg, hand or foot. In some instances, the skin surface is not located on a mucous membrane. In some instances, the skin surface is not ulcerated or bleeding. In certain instances, the skin surface has not been previously biopsied. In certain instances, the skin surface is not located on the soles of the feet or palms.

The tape stripping method, devices, and systems described herein are useful for the collection of a skin sample from a skin lesion. A skin lesion is a part of the skin that has an appearance or growth different from the surrounding skin. In some instances, the skin lesion is pigmented. A pigmented lesion includes, but is not limited to, a mole, dark colored skin spot and a melanin containing skin area. In some embodiments, the skin lesion is from about 5 mm to about 16 mm in diameter. In some instances, the skin lesion is from about 5 mm to about 15 mm, from about 5 mm to about 14 mm, from about 5 mm to about 13 mm, from about 5 mm to about 12 mm, from about 5 mm to about 11 mm, from about 5 mm to about 10 mm, from about 5 mm to about 9 mm, from about 5 mm to about 8 mm, from about 5 mm to about 7 mm, from about 5 mm to about 6 mm, from about 6 mm to about 15 mm, from about 7 mm to about 15 mm, from about 8 mm to about 15 mm, from about 9 mm to about 15 mm, from about 10 mm to about 15 mm, from about 11 mm to about 15 mm, from about 12 mm to about 15 mm, from about 13 mm to about 15 mm, from about 14 mm to about 15 mm, from about 6 to about 14 mm, from about 7 to about 13 mm, from about 8 to about 12 mm and from about 9 to about 11 mm in diameter. In some embodiments, the skin lesion is from about 10 mm to about 20 mm, from about 20 mm to about 30 mm, from about 30 mm to about 40 mm, from about 40 mm to about 50 mm, from about 50 mm to about 60 mm, from about 60 mm to about 70 mm, from about 70 mm to about 80 mm, from about 80 mm to about 90 mm, and from about 90 mm to about 100 mm in diameter. In some instances, the diameter is the longest diameter of the skin lesion. In some instances, the diameter is the smallest diameter of the skin lesion.

The adhesive skin sample collection kit comprises at least one adhesive tape, a sample collector, and an instructions for use sheet. In an exemplary embodiment, the sample collector is a tri-fold skin sample collector comprising a peelable release panel comprising at least one adhesive tape, a placement area panel comprising a removable liner, and a clear panel. The tri-fold skin sample collector may further comprise a barcode and/or an area for transcribing patient information. The adhesive skin sample collection kit is configured to include a plurality of adhesive tapes, including but not limited to 12, 11, 10, 9, 8, 7, 6, 5, 4, 3, 2, 1, from about 2 to about 8, from about 2 to about 7, from about 2 to about 6, from about 2 to about 4, from about 3 to about 6, from about 3 to about 8, from about 4 to about 10, from about 4 to about 8, from about 4 to about 6, from about 4 to about 5, from about 6 to about 10, from about 6 to about 8, or from about 4 to about 8. The instructions for use sheet provides the kit operator all of the necessary information for carrying out the tape stripping method. The instructions for use sheet preferably includes diagrams to illustrate the tape stripping method.

In some instances, the adhesive skin sample collection kit provides all the necessary components for performing the tape stripping method. In some embodiments, the adhesive skin sample collection kit includes a lab requisition form for providing patient information. In some instances, the kit further comprises accessory components. Accessory components include, but are not limited to, a marker, a resealable plastic bag, gloves and a cleansing reagent. The cleansing reagent includes, but is not limited to, an antiseptic such as isopropyl alcohol. The components of the skin sample collection kit may be provided in a cardboard box.

Tissue Sampling and Cellular Material

The methods, devices, and systems provided herein involve applying an adhesive or other similar tape to the skin in a manner so that an effective or sufficient amount of a tissue, such as a skin sample, adheres to the adhesive matrix of the adhesive tape. For example, in some embodiments, the effective or sufficient amount of a skin sample is an amount that removably adheres to a material, such as the matrix or adhesive tape. The adhered skin sample, in certain embodiments, comprises cellular material including nucleic acids and proteins. In some instances, the nucleic acid is RNA or DNA. An effective amount of a skin sample contains an amount of cellular material sufficient for performing a diagnostic assay. In some instances, the diagnostic assay is performed using the cellular material isolated from the adhered skin sample on the used adhesive tape. In some instances, the diagnostic assay is performed on the cellular material adhered to the used adhesive tape. In some embodiments, an effect amount of a skin sample comprises an amount of RNA sufficient to perform a gene expression analysis. Sufficient amounts of RNA include picogram, nanogram, and microgram quantities.

In still further or additional embodiments, the adhered skin sample comprises cellular material including nucleic acids such as RNA or DNA, or a polypeptide such as a protein, in an amount that is at least about 1 picogram. In some embodiments, the amount of cellular material is no more than about 1 nanogram. In further or additional embodiments, the amount of cellular material is no more than about 1 microgram. In still further or additional embodiments, the amount of cellular material is no more than about 1 gram.

In further or additional embodiments, the amount of cellular material is from about 1 picogram to about 1 gram. In further or additional embodiments, the cellular material comprises an amount that is from about 50 microgram to about 1 gram, from about 100 picograms to about 500 micrograms, from about 500 picograms to about 100 micrograms, from about 750 picograms to about 1 microgram, from about 1 nanogram to about 750 nanograms, or from about 1 nanogram to about 500 nanograms.

In further or additional embodiments, the amount of cellular material, including nucleic acids such as RNA or DNA, or a polypeptide such as a protein, comprises an amount that is from about 50 microgram to about 500 microgram, from about 100 microgram to about 450 microgram, from about 100 microgram to about 350 microgram, from about 100 microgram to about 300 microgram, from about 120 microgram to about 250 microgram, from about 150 microgram to about 200 microgram, from about 500 nanograms to about 5 nanograms, or from about 400 nanograms to about 10 nanograms, or from about 200 nanograms to about 15 nanograms, or from about 100 nanograms to about 20 nanograms, or from about 50 nanograms to about 10 nanograms, or from about 50 nanograms to about 25 nanograms.

In further or additional embodiments, the amount of cellular material, including nucleic acids such as RNA or DNA, or a polypeptide such as a protein, is less than about 1 gram, is less than about 500 micrograms, is less than about 490 micrograms, is less than about 480 micrograms, is less than about 470 micrograms, is less than about 460 micrograms, is less than about 450 micrograms, is less than about 440 micrograms, is less than about 430 micrograms, is less than about 420 micrograms, is less than about 410 micrograms, is less than about 400 micrograms, is less than about 390 micrograms, is less than about 380 micrograms, is less than about 370 micrograms, is less than about 360 micrograms, is less than about 350 micrograms, is less than about 340 micrograms, is less than about 330 micrograms, is less than about 320 micrograms, is less than about 310 micrograms, is less than about 300 micrograms, is less than about 290 micrograms, is less than about 280 micrograms, is less than about 270 micrograms, is less than about 260 micrograms, is less than about 250 micrograms, is less than about 240 micrograms, is less than about 230 micrograms, is less than about 220 micrograms, is less than about 210 micrograms, is less than about 200 micrograms, is less than about 190 micrograms, is less than about 180 micrograms, is less than about 170 micrograms, is less than about 160 micrograms, is less than about 150 micrograms, is less than about 140 micrograms, is less than about 130 micrograms, is less than about 120 micrograms, is less than about 110 micrograms, is less than about 100 micrograms, is less than about 90 micrograms, is less than about 80 micrograms, is less than about 70 micrograms, is less than about 60 micrograms, is less than about 50 micrograms, is less than about 20 micrograms, is less than about 10 micrograms, is less than about 5 micrograms, is less than about 1 microgram, is less than about 750 nanograms, is less than about 500 nanograms, is less than about 250 nanograms, is less than about 150 nanograms, is less than about 100 nanograms, is less than about 50 nanograms, is less than about 25 nanograms, is less than about 15 nanograms, is less than about 1 nanogram, is less than about 750 picograms, is less than about 500 picograms, is less than about 250 picograms, is less than about 100 picograms, is less than about 50 picograms, is less than about 25 picograms, is less than about 15 picograms, or is less than about 1 picogram.

Analysis of Cellular Material and Communication of Results

In some embodiments, isolated RNA from a collected skin sample is reverse transcribed into cDNA, for example for amplification by PCR to enrich for target genes. The expression levels of these target genes are quantified by quantitative PCR in a gene expression test. In some instances, in combination with quantitative PCR, a software program performed on a computer is utilized to quantify RNA isolated from the collected skin sample. In some instances, a software program or module is utilized to relate a quantity of RNA from a skin sample to a gene expression signature, wherein the gene expression signature is associated with a disease such as melanoma. In some embodiments, a software program or module scores a sample based on gene expression levels. In some embodiments, the sample score is compared with a reference sample score to determine if there is a statistical significance between the gene expression signature and a disease.

In some embodiments, one or more target genes from the isolated RNA obtained from a collected skin sample are analyzed. In some instances, from about 1 to about 100, from about 1 to about 90, from about 1 to about 80, from about 1 to about 70, from about 1 to about 60, from about 1 to about 50, from about 1 to about 40, from about 1 to about 30, from about 1 to about 20, from about 5 to about 100, from about 5 to about 80, from about 5 to about 60, from about 5 to about 40, from about 5 to about 20, from about 10 to about 100, from about 10 to about 80, from about 10 to about 60, from about 10 to about 40, from about 20 to about 80, from about 20 to about 60, from about 20 to about 40, from about 30 to about 80, from about 30 to about 60, from about 40 to about 60, from about 2 to about 10, from about 2 to about 8, or from about 2 to about 6 target genes from the isolated RNA obtained from a collected skin sample are analyzed.

In some cases, about 1, 2, 3, 4, 5, 6, 7, 8, 9, 10, 11, 12, 13, 14, 15, 20, 25, 30, 40, 50 or more target genes from the isolated RNA obtained from a collected skin sample are analyzed. In some cases, about 1 or more target genes from the isolated RNA obtained from a collected skin sample are analyzed. In some cases, about 2 or more target genes from the isolated RNA obtained from a collected skin sample are analyzed. In some cases, about 3 or more target genes from the isolated RNA obtained from a collected skin sample are analyzed. In some cases, about 4 or more target genes from the isolated RNA obtained from a collected skin sample are analyzed. In some cases, about 5 or more target genes from the isolated RNA obtained from a collected skin sample are analyzed. In some cases, about 6 or more target genes from the isolated RNA obtained from a collected skin sample are analyzed. In some cases, about 7 or more target genes from the isolated RNA obtained from a collected skin sample are analyzed. In some cases, about 8 or more target genes from the isolated RNA obtained from a collected skin sample are analyzed. In some cases, about 9 or more target genes from the isolated RNA obtained from a collected skin sample are analyzed. In some cases, about 10 or more target genes from the isolated RNA obtained from a collected skin sample are analyzed. In some cases, about 11 or more target genes from the isolated RNA obtained from a collected skin sample are analyzed. In some cases, about 12 or more target genes from the isolated RNA obtained from a collected skin sample are analyzed. In some cases, about 13 or more target genes from the isolated RNA obtained from a collected skin sample are analyzed. In some cases, about 14 or more target genes from the isolated RNA obtained from a collected skin sample are analyzed. In some cases, about 15 or more target genes from the isolated RNA obtained from a collected skin sample are analyzed. In some cases, about 20 or more target genes from the isolated RNA obtained from a collected skin sample are analyzed. In some cases, about 25 or more target genes from the isolated RNA obtained from a collected skin sample are analyzed. In some cases, about 30 or more target genes from the isolated RNA obtained from a collected skin sample are analyzed. In some cases, about 40 or more target genes from the isolated RNA obtained from a collected skin sample are analyzed. In some cases, about 50 or more target genes from the isolated RNA obtained from a collected skin sample are analyzed.

In some embodiments, the one or more target genes comprise C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some embodiments, the one or more target genes comprise a target gene selected from Table 1.

TABLE 1

| Gene Symbol | Species | Gene Name |
| --- | --- | --- |
| IL-23A | Human | interleukin 23, alpha subunit p19 |
| IL-17A | Human | interleukin 17A |
| IL-17C | Human | interleukin 17C |
| IL-17F | Human | interleukin 17F |
| TNF-α | Human | tumor necrosis factor |
| IL-17RA | Human | interleukin 17 receptor A |
| IL-17RC | Human | interleukin 17 receptor C |
| TNF RSF1A | Human | tumor necrosis factor receptor superfamily, member 1A |
| IL-6 | Human | interleukin 6 (interferon, beta 2) |
| IL-8 | Human | interleukin 8 |
| IL-21 | Human | interleukin 21 |
| IL-22 | Human | interleukin 22 |
| IL-24 | Human | interleukin 24 |
| IL-26 | Human | interleukin 26 |
| S100A7 | Human | S100 calcium binding protein A7 |
| S100A9 | Human | S100 calcium binding protein A9 |
| CCL20 | Human | chemokine (C-C motif) ligand 20 |
| CXCL1 | Human | chemokine (C-X-C motif) ligand 1 (melanoma growth stimulating activity, alpha) |
| CXCL5 | Human | chemokine (C-X-C motif) ligand 5 |
| LCN2 | Human | lipocalin 2 |
| DEFB4A | Human | defensin, beta 4A |

In some embodiments, the one or more target genes comprise C6orf218, preferentially expressed antigen in melanoma (PRAME), or a combination thereof. In some cases, the one or more target genes comprise C6orf218. In other cases, the one or more target genes comprise preferentially expressed antigen in melanoma (PRAME).

In some embodiments, one or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some instances, from about 1 to about 100, from about 1 to about 90, from about 1 to about 80, from about 1 to about 70, from about 1 to about 60, from about 1 to about 50, from about 1 to about 40, from about 1 to about 30, from about 1 to about 20, from about 5 to about 100, from about 5 to about 80, from about 5 to about 60, from about 5 to about 40, from about 5 to about 20, from about 10 to about 100, from about 10 to about 80, from about 10 to about 60, from about 10 to about 40, from about 20 to about 80, from about 20 to about 60, from about 20 to about 40, from about 30 to about 80, from about 30 to about 60, from about 40 to about 60, from about 2 to about 10, from about 2 to about 8, or from about 2 to about 6 target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof.

In some cases, about 1, 2, 3, 4, 5, 6, 7, 8, 9, 10, 11, 12, 13, 14, 15, 20, 25, 30, 40, 50 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 1 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 2 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 3 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 4 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof.

In some cases, about 5 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 6 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 7 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 8 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 9 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 10 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, ora combination thereof. In some cases, about 11 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 12 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 13 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, ora combination thereof. In some cases, about 14 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 15 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 20 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 25 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 30 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof. In some cases, about 40 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, ora combination thereof. In some cases, about 50 or more target genes from the isolated RNA obtained from a collected skin sample are analyzed, in which the one or more target genes comprise at least C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof.

In some embodiments, one or more target genes from the isolated RNA obtained from a collected skin sample are analyzed, in which the one or more target genes comprise at least one target gene selected from Table 1. In some instances, from about 1 to about 100, from about 1 to about 90, from about 1 to about 80, from about 1 to about 70, from about 1 to about 60, from about 1 to about 50, from about 1 to about 40, from about 1 to about 30, from about 1 to about 20, from about 5 to about 100, from about 5 to about 80, from about 5 to about 60, from about 5 to about 40, from about 5 to about 20, from about 10 to about 100, from about 10 to about 80, from about 10 to about 60, from about 10 to about 40, from about 20 to about 80, from about 20 to about 60, from about 20 to about 40, from about 30 to about 80, from about 30 to about 60, from about 40 to about 60, from about 2 to about 10, from about 2 to about 8, or from about 2 to about 6 target genes from the isolated RNA obtained from a collected skin sample are analyzed, in which the one or more target genes comprise at least one target gene selected from Table 1.

In some cases, about 1, 2, 3, 4, 5, 6, 7, 8, 9, 10, 11, 12, 13, 14, 15, 20, 25, 30, 40, 50 or more target genes from the isolated RNA obtained from a collected skin sample are analyzed, in which the one or more target genes comprise at least one target gene selected from Table 1. In some cases, about 1 or more target genes from the isolated RNA obtained from a collected skin sample are analyzed, in which the one or more target genes comprise at least one target gene selected from Table 1. In some cases, about 2 or more target genes from the isolated RNA obtained from a collected skin sample are analyzed, in which the one or more target genes comprise at least one target gene selected from Table 1. In some cases, about 3 or more target genes from the isolated RNA obtained from a collected skin sample are analyzed, in which the one or more target genes comprise at least one target gene selected from Table 1. In some cases, about 4 or more target genes from the isolated RNA obtained from a collected skin sample are analyzed, in which the one or more target genes comprise at least one target gene selected from Table 1. In some cases, about 5 or more target genes from the isolated RNA obtained from a collected skin sample are analyzed, in which the one or more target genes comprise at least one target gene selected from Table 1. In some cases, about 6 or more target genes from the isolated RNA obtained from a collected skin sample are analyzed, in which the one or more target genes comprise at least one target gene selected from Table 1. In some cases, about 7 or more target genes from the isolated RNA obtained from a collected skin sample are analyzed, in which the one or more target genes comprise at least one target gene selected from Table 1. In some cases, about 8 or more target genes from the isolated RNA obtained from a collected skin sample are analyzed, in which the one or more target genes comprise at least one target gene selected from Table 1. In some cases, about 9 or more target genes from the isolated RNA obtained from a collected skin sample are analyzed, in which the one or more target genes comprise at least one target gene selected from Table 1. In some cases, about 10 or more target genes from the isolated RNA obtained from a collected skin sample are analyzed, in which the one or more target genes comprise at least one target gene selected from Table 1. In some cases, about 11 or more target genes from the isolated RNA obtained from a collected skin sample are analyzed, in which the one or more target genes comprise at least one target gene selected from Table 1. In some cases, about 12 or more target genes from the isolated RNA obtained from a collected skin sample are analyzed, in which the one or more target genes comprise at least one target gene selected from Table 1. In some cases, about 13 or more target genes from the isolated RNA obtained from a collected skin sample are analyzed, in which the one or more target genes comprise at least one target gene selected from Table 1. In some cases, about 14 or more target genes from the isolated RNA obtained from a collected skin sample are analyzed, in which the one or more target genes comprise at least one target gene selected from Table 1. In some cases, about 15 or more target genes from the isolated RNA obtained from a collected skin sample are analyzed, in which the one or more target genes comprise at least one target gene selected from Table 1. In some cases, about 20 or more target genes from the isolated RNA obtained from a collected skin sample are analyzed, in which the one or more target genes comprise at least one target gene selected from Table 1. In some cases, about 25 or more target genes from the isolated RNA obtained from a collected skin sample are analyzed, in which the one or more target genes comprise at least one target gene selected from Table 1. In some cases, about 30 or more target genes from the isolated RNA obtained from a collected skin sample are analyzed, in which the one or more target genes comprise at least one target gene selected from Table 1. In some cases, about 40 or more target genes from the isolated RNA obtained from a collected skin sample are analyzed, in which the one or more target genes comprise at least one target gene selected from Table 1. In some cases, about 50 or more target genes from the isolated RNA obtained from a collected skin sample are analyzed, in which the one or more target genes comprise at least one target gene selected from Table 1.

In some embodiments, one or more target genes from the isolated RNA obtained from a collected skin sample are analyzed, in which the one or more target genes comprise at least C6orf218, preferentially expressed antigen in melanoma (PRAME), or a combination thereof. In some instances, from about 1 to about 100, from about 1 to about 90, from about 1 to about 80, from about 1 to about 70, from about 1 to about 60, from about 1 to about 50, from about 1 to about 40, from about 1 to about 30, from about 1 to about 20, from about 5 to about 100, from about 5 to about 80, from about 5 to about 60, from about 5 to about 40, from about 5 to about 20, from about 10 to about 100, from about 10 to about 80, from about 10 to about 60, from about 10 to about 40, from about 20 to about 80, from about 20 to about 60, from about 20 to about 40, from about 30 to about 80, from about 30 to about 60, from about 40 to about 60, from about 2 to about 10, from about 2 to about 8, or from about 2 to about 6 target genes from the isolated RNA obtained from a collected skin sample are analyzed, in which the one or more target genes comprise at least C6orf218, preferentially expressed antigen in melanoma (PRAME), or a combination thereof.

In some cases, about 1, 2, 3, 4, 5, 6, 7, 8, 9, 10, 11, 12, 13, 14, 15, 20, 25, 30, 40, 50 or more target genes from the isolated RNA obtained from a collected skin sample are analyzed, in which the one or more target genes comprise at least C6orf218, preferentially expressed antigen in melanoma (PRAME), or a combination thereof. In some cases, about 1 or more target genes from the isolated RNA obtained from a collected skin sample are analyzed, in which the one or more target genes comprise at least C6orf218, preferentially expressed antigen in melanoma (PRAME), or a combination thereof. In some cases, about 2 or more target genes from the isolated RNA obtained from a collected skin sample are analyzed, in which the one or more target genes comprise at least C6orf218, preferentially expressed antigen in melanoma (PRAME), or a combination thereof. In some cases, about 3 or more target genes from the isolated RNA obtained from a collected skin sample are analyzed, in which the one or more target genes comprise at least C6orf218, preferentially expressed antigen in melanoma (PRAME), or a combination thereof. In some cases, about 4 or more target genes from the isolated RNA obtained from a collected skin sample are analyzed, in which the one or more target genes comprise at least C6orf218, preferentially expressed antigen in melanoma (PRAME), or a combination thereof. In some cases, about 5 or more target genes from the isolated RNA obtained from a collected skin sample are analyzed, in which the one or more target genes comprise at least C6orf218, preferentially expressed antigen in melanoma (PRAME), or a combination thereof. In some cases, about 6 or more target genes from the isolated RNA obtained from a collected skin sample are analyzed, in which the one or more target genes comprise at least C6orf218, preferentially expressed antigen in melanoma (PRAME), or a combination thereof. In some cases, about 7 or more target genes from the isolated RNA obtained from a collected skin sample are analyzed, in which the one or more target genes comprise at least C6orf218, preferentially expressed antigen in melanoma (PRAME), or a combination thereof. In some cases, about 8 or more target genes from the isolated RNA obtained from a collected skin sample are analyzed, in which the one or more target genes comprise at least C6orf218, preferentially expressed antigen in melanoma (PRAME), or a combination thereof. In some cases, about 9 or more target genes from the isolated RNA obtained from a collected skin sample are analyzed, in which the one or more target genes comprise at least C6orf218, preferentially expressed antigen in melanoma (PRAME), or a combination thereof. In some cases, about 10 or more target genes from the isolated RNA obtained from a collected skin sample are analyzed, in which the one or more target genes comprise at least C6orf218, preferentially expressed antigen in melanoma (PRAME), or a combination thereof. In some cases, about 11 or more target genes from the isolated RNA obtained from a collected skin sample are analyzed, in which the one or more target genes comprise at least C6orf218, preferentially expressed antigen in melanoma (PRAME), or a combination thereof. In some cases, about 12 or more target genes from the isolated RNA obtained from a collected skin sample are analyzed, in which the one or more target genes comprise at least C6orf218, preferentially expressed antigen in melanoma (PRAME), or a combination thereof. In some cases, about 13 or more target genes from the isolated RNA obtained from a collected skin sample are analyzed, in which the one or more target genes comprise at least C6orf218, preferentially expressed antigen in melanoma (PRAME), or a combination thereof. In some cases, about 14 or more target genes from the isolated RNA obtained from a collected skin sample are analyzed, in which the one or more target genes comprise at least C6orf218, preferentially expressed antigen in melanoma (PRAME), or a combination thereof. In some cases, about 15 or more target genes from the isolated RNA obtained from a collected skin sample are analyzed, in which the one or more target genes comprise at least C6orf218, preferentially expressed antigen in melanoma (PRAME), or a combination thereof. In some cases, about 20 or more target genes from the isolated RNA obtained from a collected skin sample are analyzed, in which the one or more target genes comprise at least C6orf218, preferentially expressed antigen in melanoma (PRAME), or a combination thereof. In some cases, about 25 or more target genes from the isolated RNA obtained from a collected skin sample are analyzed, in which the one or more target genes comprise at least C6orf218, preferentially expressed antigen in melanoma (PRAME), or a combination thereof. In some cases, about 30 or more target genes from the isolated RNA obtained from a collected skin sample are analyzed, in which the one or more target genes comprise at least C6orf218, preferentially expressed antigen in melanoma (PRAME), or a combination thereof. In some cases, about 40 or more target genes from the isolated RNA obtained from a collected skin sample are analyzed, in which the one or more target genes comprise at least C6orf218, preferentially expressed antigen in melanoma (PRAME), or a combination thereof. In some cases, about 50 or more target genes from the isolated RNA obtained from a collected skin sample are analyzed, in which the one or more target genes comprise at least C6orf218, preferentially expressed antigen in melanoma (PRAME), or a combination thereof.

In some embodiments, one or more target genes from the isolated RNA obtained from a collected skin sample are analyzed, in which the one or more target genes comprise at least C6orf218. In some instances, from about 1 to about 100, from about 1 to about 90, from about 1 to about 80, from about 1 to about 70, from about 1 to about 60, from about 1 to about 50, from about 1 to about 40, from about 1 to about 30, from about 1 to about 20, from about 5 to about 100, from about 5 to about 80, from about 5 to about 60, from about 5 to about 40, from about 5 to about 20, from about 10 to about 100, from about 10 to about 80, from about 10 to about 60, from about 10 to about 40, from about 20 to about 80, from about 20 to about 60, from about 20 to about 40, from about 30 to about 80, from about 30 to about 60, from about 40 to about 60, from about 2 to about 10, from about 2 to about 8, or from about 2 to about 6 target genes from the isolated RNA obtained from a collected skin sample are analyzed, in which the one or more target genes comprise at least C6orf218.

In some cases, about 1, 2, 3, 4, 5, 6, 7, 8, 9, 10, 11, 12, 13, 14, 15, 20, 25, 30, 40, 50 or more target genes from the isolated RNA obtained from a collected skin sample are analyzed, in which the one or more target genes comprise at least C6orf218. In some cases, about 1 or more target genes from the isolated RNA obtained from a collected skin sample are analyzed, in which the one or more target genes comprise at least C6orf218. In some cases, about 2 or more target genes from the isolated RNA obtained from a collected skin sample are analyzed, in which the one or more target genes comprise at least C6orf218. In some cases, about 3 or more target genes from the isolated RNA obtained from a collected skin sample are analyzed, in which the one or more target genes comprise at least C6orf218. In some cases, about 4 or more target genes from the isolated RNA obtained from a collected skin sample are analyzed, in which the one or more target genes comprise at least C6orf218. In some cases, about 5 or more target genes from the isolated RNA obtained from a collected skin sample are analyzed, in which the one or more target genes comprise at least C6orf218. In some cases, about 6 or more target genes from the isolated RNA obtained from a collected skin sample are analyzed, in which the one or more target genes comprise at least C6orf218. In some cases, about 7 or more target genes from the isolated RNA obtained from a collected skin sample are analyzed, in which the one or more target genes comprise at least C6orf218. In some cases, about 8 or more target genes from the isolated RNA obtained from a collected skin sample are analyzed, in which the one or more target genes comprise at least C6orf218. In some cases, about 9 or more target genes from the isolated RNA obtained from a collected skin sample are analyzed, in which the one or more target genes comprise at least C6orf218. In some cases, about 10 or more target genes from the isolated RNA obtained from a collected skin sample are analyzed, in which the one or more target genes comprise at least C6orf218. In some cases, about 11 or more target genes from the isolated RNA obtained from a collected skin sample are analyzed, in which the one or more target genes comprise at least C6orf218. In some cases, about 12 or more target genes from the isolated RNA obtained from a collected skin sample are analyzed, in which the one or more target genes comprise at least C6orf218. In some cases, about 13 or more target genes from the isolated RNA obtained from a collected skin sample are analyzed, in which the one or more target genes comprise at least C6orf218. In some cases, about 14 or more target genes from the isolated RNA obtained from a collected skin sample are analyzed, in which the one or more target genes comprise at least C6orf218. In some cases, about 15 or more target genes from the isolated RNA obtained from a collected skin sample are analyzed, in which the one or more target genes comprise at least C6orf218. In some cases, about 20 or more target genes from the isolated RNA obtained from a collected skin sample are analyzed, in which the one or more target genes comprise at least C6orf218. In some cases, about 25 or more target genes from the isolated RNA obtained from a collected skin sample are analyzed, in which the one or more target genes comprise at least C6orf218. In some cases, about 30 or more target genes from the isolated RNA obtained from a collected skin sample are analyzed, in which the one or more target genes comprise at least C6orf218. In some cases, about 40 or more target genes from the isolated RNA obtained from a collected skin sample are analyzed, in which the one or more target genes comprise at least C6orf218. In some cases, about 50 or more target genes from the isolated RNA obtained from a collected skin sample are analyzed, in which the one or more target genes comprise at least C6orf218.

The subject matter described herein, including the gene expression tests and corresponding transmission of data, in certain aspects, are configured to be performed in one or more facilities at one or more locations. Facility locations are not limited by country and include any country or territory. Facility locations are not limited by country and include any country or territory. In some instances, one or more steps of the gene expression test are performed in a different country than another step of the gene expression test. In some instances, one or more steps of the gene expression test are performed in a different country than one or more steps of the tape stripping aspect. In some embodiments, one or more articles are transferred from one or more of the facilities to one or more different facilities for analysis or further analysis. An article includes, but is not limited to, one or more components of the skin sample collection kit, a used adhesive tape, isolated cellular material obtained from a used adhesive tape, processed cellular material, and/or data. Processed cellular material includes, but is not limited to, cDNA reverse transcribed from RNA, amplified RNA, and amplified cDNA. Data includes, but is not limited to, information regarding the expression level of one or more target genes, information regarding a gene expression signature, and information regarding a disease, such as melanoma. In some embodiments of the methods, devices, and systems described herein, the analysis is performed and a subsequent data transmission step will convey or transmit the results of the analysis. Information regarding a disease, includes, but is not limited to, identification of a disease state, likelihood of treatment success for a given disease state, identification of progression of a disease state (e.g., invasiveness of melanoma), and identification of a disease stage (e.g., melanoma stages 0, 1, 2, 3, or 4).

In certain examples, the application of the adhesive tape to a skin sample comprises holding the skin taut and pressing the adhesive tape firmly on the skin surface while making circular motions on the tape. Between about 1 and about 20, between about 1 and about 15, between about 1 and about 10, between about 1 and about 5, between about 5 and about 20, between about 10 and about 20, and between about 10 and 15 circular motions are made on the tape. In one embodiment, about 15 circular motions are made on the tape. In some embodiments, the tape is configured to remain on the skin surface for up to 6, 5, 4, 3, 2, and 1 minutes. After firm application to the skin, the tape is slowly removed in one direction. In certain aspects, the tape stripping method further comprises demarcating the sampled skin region on a second surface of a transparent adhesive tape, wherein the first surface is the skin facing surface comprising the adhesive matrix. The demarcation indicates the sample region to be processed. The demarcation may be the outline of a skin lesion. The marker used for demarcation may be provided in the skin sample collection kit.

In some embodiments of the subject matter described herein, the adhesive skin sample collection kit comprises a self-addressed package for delivery of one or more used adhesive tapes to a facility. In some instances, the package includes a prepaid shipping label. In some embodiments, the facility is a facility which will perform one or more diagnostic steps or procedures involving the cellular material adhered to the one or more used adhesive tapes. In some embodiments, the one or more diagnostic procedures includes, but is not limited to, any step performed in a gene expression test (e.g., a pigmented lesion assay), immunohistochemistry assay, immunophenotyping, ELISA, fluorescent in situ hybridization (FISH), and/or gene sequencing. The facility where any diagnostic procedure or tape stripping method described herein is performed is not limited to one country. In some instances, one or more diagnostic procedures or tape stripping methods are performed in one or more different countries. In some embodiments, a diagnostic procedure includes data analysis for any step of any diagnostic procedure described herein. In some embodiments, any step of any diagnostic procedure described herein is performed by a software program or module on a computer. In additional or further embodiments, data from any step of any procedure described herein is transferred to and from facilities located within the same or different countries, including analysis performed in one facility in a particular location and the data shipped to another location or directly to an individual in the same or a different country. In additional or further embodiments, data from any step of any procedure described herein (including analysis of cellular material such as DNA, RNA, and protein as well as transformed data from cellular material) is transferred to and/or received from a facility located within the same or different countries, including analysis of a data input, such as cellular material, performed in one facility in a particular location and corresponding data transmitted to another location, or directly to an individual, such as data related to the diagnosis, prognosis, responsiveness to therapy, or the like, in the same or different location or country.

The adhesive skin sample collection kit is configured so that the tape stripping method may be performed by a variety of operators in a variety of locations. In some embodiments, the method is performed in a clinician's office, an outpatient facility or at a home. The method is not limited to use in a facility and is configured to be utilized in a variety of locales.

The method may is performed by a practitioner, nurse or any individual who has read and understood the instructions for use and is capable of performing the method according to the instructions for use sheet.

In some instances, the skin sample collection kit is used in combination with skin condition monitoring. For example, images of the skin sample tested are captured and stored on a mobile photoinformatic platform that maintains the images with the associated clinical information and data relating to the skin lesion sampled.

Computer Program

The methods, software, media, and systems disclosed herein comprise at least one computer processor, or use of the same. The computer processor may comprise a computer program. A computer program may include a sequence of instructions, executable in the digital processing device's CPU, written to perform a specified task. Computer readable instructions may be implemented as program modules, such as functions, features, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. A computer program may comprise one sequence of instructions. A computer program may comprise a plurality of sequences of instructions. A computer program may be provided from one location. A computer program may be provided from a plurality of locations. A computer program may include one or more software modules. A computer program may include, in part or in whole, one or more web applications, one or more mobile applications, one or more standalone applications, one or more web browser plug-ins, extensions, add-ins, or add-ons, or combinations thereof.

Web Application

A computer program may include a web application. In light of the disclosure provided herein, those of skill in the art will recognize that a web application may utilize one or more software frameworks and one or more database systems. A web application may be created upon a software framework such as Microsoft® .NET or Ruby on Rails (RoR). A web application may utilize one or more database systems including, by way of non-limiting examples, relational, non-relational, feature oriented, associative, and XML database systems. Suitable relational database systems may include, by way of non-limiting examples, Microsoft® SQL Server, mySQL™, and Oracle®. Those of skill in the art will also recognize that a web application may be written in one or more versions of one or more languages. A web application may be written in one or more markup languages, presentation definition languages, client-side scripting languages, server-side coding languages, database query languages, or combinations thereof. A web application may be written to some extent in a markup language such as Hypertext Markup Language (HTML), Extensible Hypertext Markup Language (XHTML), or eXtensible Markup Language (XML). A web application may be written to some extent in a presentation definition language such as Cascading Style Sheets (CSS). A web application may be written to some extent in a client-side scripting language such as Asynchronous Javascript and XML (AJAX), Flash® Actionscript, Javascript, or Silverlight®. A web application may be written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. A web application may be written to some extent in a database query language such as Structured Query Language (SQL). A web application may integrate enterprise server products such as IBM® Lotus Domino®. A web application may include a media player element. A media player element may utilize one or more of many suitable multimedia technologies including, by way of non-limiting examples, Adobe® Flash®, HTML 5, Apple® QuickTime®, Microsoft® Silverlight®, Java™, and Unity®.

Mobile Application

A computer program may include a mobile application provided to a mobile digital processing device. The mobile application may be provided to a mobile digital processing device at the time it is manufactured. The mobile application may be provided to a mobile digital processing device via the computer network described herein.

A mobile application may be created by techniques known to those of skill in the art using hardware, languages, and development environments known to the art. Those of skill in the art will recognize that mobile applications may be written in several languages. Suitable programming languages include, by way of non-limiting examples, C, C++, C#, Featureive-C, Java™, Javascript, Pascal, Feature Pascal, Python™, Ruby, VB.NET, WML, and XHTML/HTML with or without CSS, or combinations thereof.

Suitable mobile application development environments may be available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments may be available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums may be available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

A computer program may include a standalone application, which may be a program that may be run as an independent computer process, not an add-on to an existing process, e.g., not a plug-in. Those of skill in the art will recognize that standalone applications may be often compiled. A compiler may be a computer program(s) that transforms source code written in a programming language into binary feature code such as assembly language or machine code. Suitable compiled programming languages include, by way of non-limiting examples, C, C++, Featureive-C, COBOL, Delphi, Eiffel, Java™, Lisp, Python™, Visual Basic, and VB .NET, or combinations thereof. Compilation may be often performed, at least in part, to create an executable program. A computer program may include one or more executable complied applications.

Web Browser Plug-in

A computer program may include a web browser plug-in. In computing, a plug-in may be one or more software components that add specific functionality to a larger software application. Makers of software applications may support plug-ins to enable third-party developers to create abilities which extend an application, to support easily adding new features, and to reduce the size of an application. When supported, plug-ins may enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. The toolbar may comprise one or more web browser extensions, add-ins, or add-ons. The toolbar may comprise one or more explorer bars, tool bands, or desk bands.

In view of the disclosure provided herein, those of skill in the art will recognize that several plug-in frameworks may be available that enable development of plug-ins in various programming languages, including, by way of non-limiting examples, C++, Delphi, Java™, PHP, Python™, and VB .NET, or combinations thereof.

Web browsers (also called Internet browsers) may be software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. The web browser may be a mobile web browser. Mobile web browsers (also called mircrobrowsers, mini-browsers, and wireless browsers) may be designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The medium, method, and system disclosed herein comprise one or more softwares, servers, and database modules, or use of the same. In view of the disclosure provided herein, software modules may be created by techniques known to those of skill in the art using machines, software, and languages known to the art. The software modules disclosed herein may be implemented in a multitude of ways. A software module may comprise a file, a section of code, a programming feature, a programming structure, or combinations thereof. A software module may comprise a plurality of files, a plurality of sections of code, a plurality of programming features, a plurality of programming structures, or combinations thereof. The one or more software modules may comprise, by way of non-limiting examples, a web application, a mobile application, and a standalone application. Software modules may be in one computer program or application. Software modules may be in more than one computer program or application. Software modules may be hosted on one machine. Software modules may be hosted on more than one machine. Software modules may be hosted on cloud computing platforms. Software modules may be hosted on one or more machines in one location. Software modules may be hosted on one or more machines in more than one location.

Databases

The medium, method, and system disclosed herein comprise one or more databases, or use of the same. In view of the disclosure provided herein, those of skill in the art will recognize that many databases may be suitable for storage and retrieval of geologic profile, operator activities, division of interest, and/or contact information of royalty owners. Suitable databases may include, by way of non-limiting examples, relational databases, non-relational databases, feature oriented databases, feature databases, entity-relationship model databases, associative databases, and XML databases. A database may be internet-based. A database may be web-based. A database may be cloud computing-based. A database may be based on one or more local computer storage devices.

EXAMPLES

Example 1: Point of Care Skin Sample Collection

A pigmented lesion located on the hand of a subject is selected for skin sampling. The skin sampling area contains a minimal amount of hair, is not irritated and has not been previously biopsied. The lesion is about 8 mm in size. As exemplified in FIG. 1, the skin sampling area (101) comprising the skin lesion (102) is cleansed with an alcohol pad (103) by a practitioner (104) wearing gloves, and the skin is allowed to air dry for 5 minutes.

Figure 2:
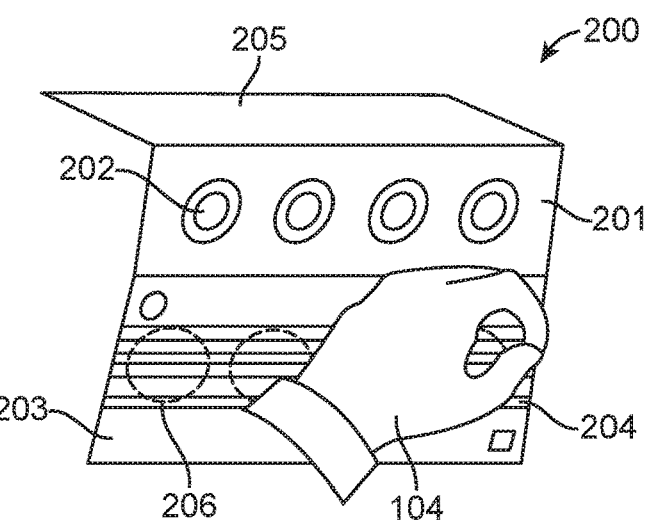
FIG. 2 is illustrative of a tri-fold skin sample collector comprising a peelable release panel comprising four adhesive tapes, a placement area panel comprising a removable liner, and a clear panel.
Figure 8:
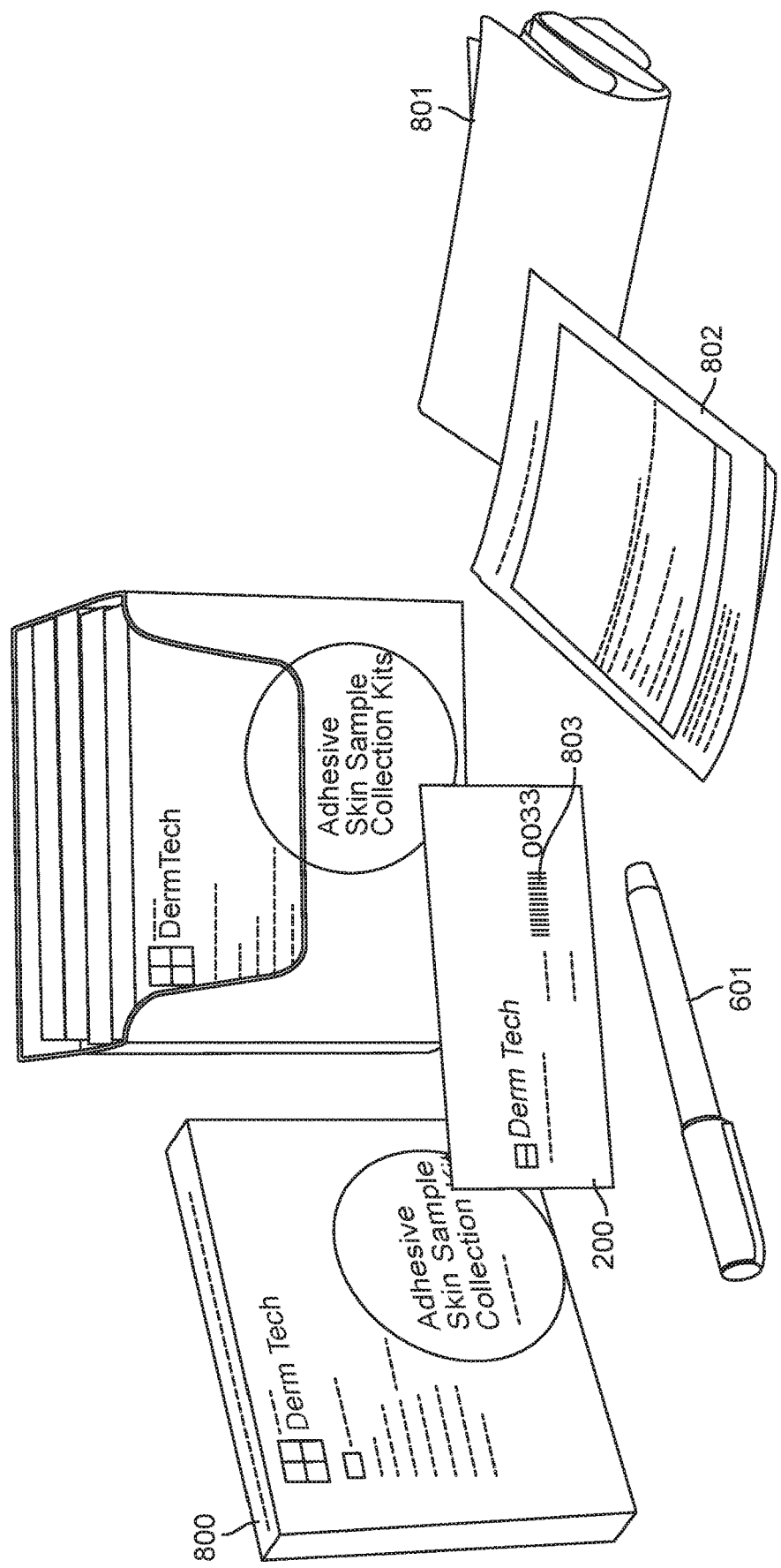
FIG. 8 is illustrative of an adhesive skin sample collection kit.

A tri-fold skin sample collector is removed from an adhesive skin sample collection kit exemplified by FIG. 8. FIG. 2 exemplifies the tri-fold skin sample collector (200) comprising a peelable release panel (201) comprising four adhesive tapes (202), a placement area panel (203) comprising a removable liner (204), and a clear panel (205). The tri-fold skin sample collector has a barcode specific for the subject. The removable liner is removed from the placement area panel (203), exposing four regions (206) designated for the placement of up to four used adhesive tapes. The four regions of the placement area panel are not exposed to any skin prior to application of a used tape.

Figure 3:
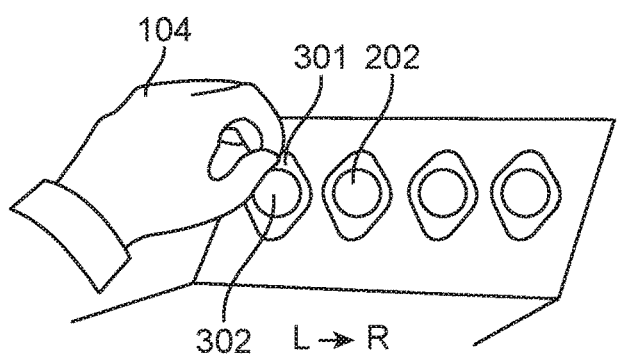
FIG. 3 is illustrates removing a first adhesive tape positioned at the far left side of a peelable release panel of a tri-fold skin sample collector.
Figure 4:
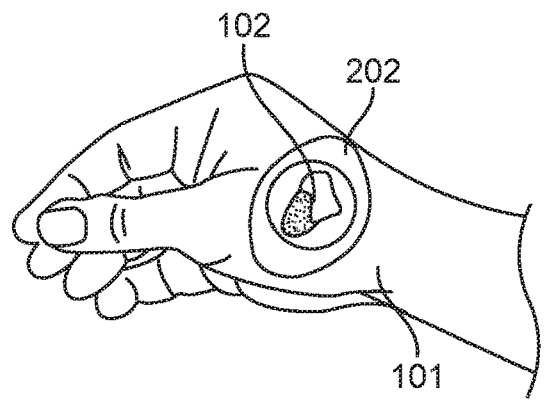
FIG. 4 is illustrative of an adhesive tape positioned on a cleansed skin sampling area comprising a skin lesion.
Figure 5:
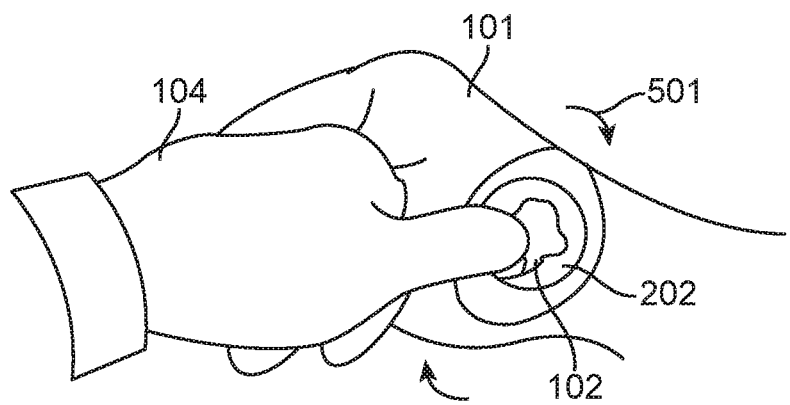
FIG. 5 illustrates pressing firmly on an adhesive tape positioned on a cleansed skin sampling area while making a circular motion.
Figure 6:
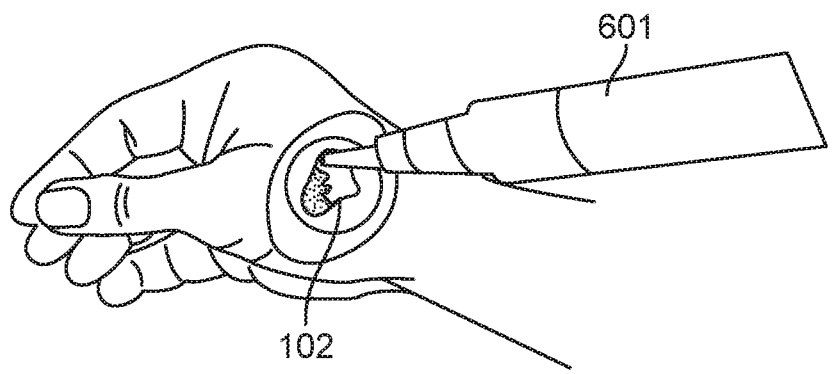
FIG. 6 is illustrative of demarcating a region comprising a skin lesion on an adhesive tape.
Figure 7:
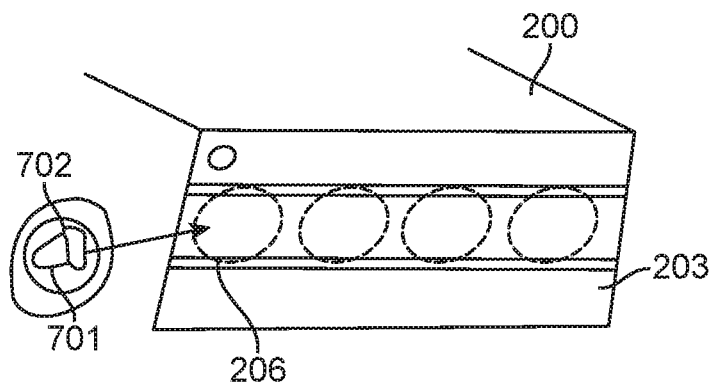
FIG. 7 is illustrative of placing a used adhesive tape comprising a skin sample onto a placement area panel of a tri-fold skin sample collector.

An adhesive tape is removed from the top left side of the peelable release panel as exemplified in FIG. 3. The practitioner (104) handles the adhesive tape (202) by the tab region (301) so that the matrix material of the central collection area (302) does not come in contact with a surface prior to skin application. The skin sampling area is held taut while the adhesive tape is applied onto the skin sampling area. An adhesive tape (202) positioned on the cleansed skin sampling area (101) comprising a skin lesion (102) is exemplified in FIG. 4. The adhesive tape is pressed firmly on the skin while making 15 circular motions. FIG. 5 exemplifies the practitioner (104) pressing on the skin comprising a skin lesion (102) while making a circular motion (501). As exemplified in FIG. 6, the lesion area (102) is demarcated on the adhesive tape (202) using a marker (601) provided in the skin sample collection kit exemplified in Example 8. The practitioner slowly removes the used adhesive tape from the skin sampling area by holding the tab and pulling in one direction. The used tape (701) comprising a skin sample (702) is placed on the first unoccupied skin collection region (206) of the placement area panel (203) on the tri-fold skin sample collector (200) as exemplified in FIG. 7. The procedure is repeated with three additional tapes on the same lesion.

The tri-fold skin sample collector is folded and placed in a package provided with the skin sample collection kit. The package contains pre-paid postage and is self-addressed to a processing facility.

Example 2: Skin Sample Collection

A pigmented lesion located on the upper back of a subject is selected for skin sampling. The skin sampling area contains a minimal amount of hair, is not irritated and has not been previously biopsied. The lesion is about 15 mm in size. The lesion is sampled utilizing an adhesive skin sample collection kit. The skin sample collection kit includes an instructions for use sheet (or an instruction manual). The lesion is sampled by a capable person who has read and understood the skin sample collection kit instructions for use sheet.

A pair of gloves is removed from the skin sample collection kit and the fitted onto the person performing the skin sampling procedure. The skin sampling area comprising the pigmented lesion is cleansed with an alcohol pad provided in the adhesive skin sample collection kit and the skin is allowed to air dry.

A tri-fold skin sample collector is removed from the adhesive skin sample collection kit. The tri-fold skin sample collector comprises a peelable release panel comprising four adhesive tapes, a placement area panel comprising a removable liner, and a clear panel. The tri-fold skin sample collector has a barcode specific for the subject. The tri-fold skin sample collector further comprises an area configured for providing patient information. The tri-fold skin sample collector is labeled with the subject's name and identifying information. The removable liner is removed from the placement area panel, exposing four regions designated for the placement of up to four used adhesive tapes. The four regions of the placement area panel are not exposed to any skin prior to application of a used tape.

An adhesive tape is removed from the top left side of the peelable release panel. The adhesive tape is handled by the tab region so that the matrix material does not come in contact with a surface prior to skin application. The skin is held taut while the adhesive tape is applied onto the skin sampling area. The adhesive tape is pressed firmly on the skin while making 10 circular motions. The lesion area is demarcated on the adhesive tape using a marker provided in the adhesive skin sample collection kit. The used tape is slowly removed in one direction by pulling the tab away from the skin. The used tape is placed on the first unoccupied skin collection region of the tri-fold skin sample collector. The skin sample procedure is repeated with three additional tapes on the same skin lesion.

The tri-fold skin sample collector comprising 4 used adhesive tapes is folded and placed in the package provided with the adhesive skin sample collection kit. The package contains pre-paid postage and is self-addressed to a diagnostics facility.

Example 3: Collection System

The adhesive skin sample collection kit components are stored in a cardboard box (800) as exemplified in FIG. 8. The kit contains a tri-fold skin sample collector (200) comprising four adhesive tapes, instructions for use sheet, a marking pen, a pre-paid, self-addressed shipping package (801), and a shipping label (802). The tri-fold skin sample collector comprises three panels including a peelable release panel comprising the four adhesive tapes, a placement area panel comprising a removable liner and a clear panel. The tri-fold skin sample collector further comprises a unique barcode (803) configured to identify a subject. The adhesive tapes stored on the peelable release panel have an expiry date of 2 years from the date of manufacture. The skin sample collection kit is stored between 10® C. and 30® C. The instructions for use sheet (or instruction manual) include all information necessary to enable a person to understand and perform the method. The instructions for use sheet (or instruction manual) include diagrams describing steps of the skin sample collection method.

The examples and embodiments described herein are for illustrative purposes only and various modifications or changes suggested to persons skilled in the art are to be included within the spirit and purview of this application and scope of the appended claims.

What is claimed is:

1. A tri-fold skin sample collector, comprising:
   a peelable release panel comprising 2 to 12 adhesive tapes, wherein each of the adhesive tapes are configured for application to a skin surface; and
   a placement area panel comprising a removable liner and 2 to 12 regions, wherein each of the 2 to 12 regions is designated for the placement of a used adhesive tape,
   wherein each of the adhesive tapes comprises an adhesive matrix,
   wherein the adhesive matrix is configured to adhere to an effective amount of a skin sample,
   wherein the effective amount of the skin sample comprises from about 50 microgram to about 1 gram of cellular material.

2. The tri-fold skin sample collector of claim 1, wherein the tri-fold sample collector is labeled with a unique barcode that is assigned to a patient sample.

3. The tri-fold skin sample collector of claim 1, wherein the peelable release panel is configured to hold between 4 to 10 adhesive tapes, between 6 to 10 adhesive tapes, between 6 to 8 adhesive tapes, or between 4 to 8 adhesive tapes.

4. The tri-fold skin sample collector of claim 1, wherein the placement area panel is configured to hold between 4 to 10 adhesive tapes, between 6 to 10 adhesive tapes, between 6 to 8 adhesive tapes, or between 4 to 8 adhesive tapes.

5. The tri-fold skin sample collector of claim 1, wherein the peelable release panel is configured to hold 4 adhesive tapes and the placement area panel is configured to hold 4 adhesive tapes.

6. The tri-fold skin sample collector of claim 1, wherein the peelable release panel is configured to hold 8 adhesive tapes and the placement area panel is configured to hold 8 adhesive tapes.

7. The tri-fold skin sample collector of claim 1, wherein the cellular material is a nucleic acid.

8. The tri-fold skin sample collector of claim 7, wherein the cellular material is RNA or DNA.

9. The tri-fold skin sample collector of claim 1, wherein that the effective amount of the skin sample comprises between about 50 microgram to about 500 microgram, between about 100 microgram to about 450 microgram, between about 100 microgram to about 350 microgram, between about 100 microgram to about 300 microgram, between about 120 microgram to about 250 microgram, or between about 150 microgram to about 200 microgram of RNA material.

10. The tri-fold skin sample collector of claim 1, wherein the adhesive tape does not comprise a latex material, a silicone material, or a combination thereof.

11. The tri-fold skin sample collector of claim 1, wherein the adhesive matrix is comprised of a synthetic rubber compound.

12. The tri-fold skin sample collector of claim 1, wherein the adhesive tape is comprised of a transparent and/or flexible material.

13. The tri-fold skin sample collector of claim 1, wherein the adhesive tape comprises a first central collection area having a skin facing surface comprising the adhesive matrix and a second area extending from the periphery of the first collection area creating a tab.

14. The tri-fold skin sample collector of claim 13, wherein the first central collection area and the second area are comprised of different materials.

15. The tri-fold skin sample collector of claim 13, wherein the first central collection area:
   is comprised of a polyurethane carrier film;
   has an elliptical shape; or
   has a second surface for demarcation of a zone around a skin lesion.

16. The tri-fold skin sample collector of claim 13, wherein the longest length of the first central collection area is from about 5 mm to about 50 mm.

17. A non-invasive method for isolating a skin sample, comprising:
   a) applying an adhesive tape from a tri-fold skin sample collector of claim 1 to a desired skin surface, provided that a skin sample adheres to the adhesive matrix; and
   b) removing the adhesive tape thereby stripping an adhered skin sample from the skin surface.

18. The method of claim 17, wherein the skin surface is prepared for skin sampling by removing any hairs on the skin surface, cleansing the surface with an antiseptic, drying the surface completely prior to application of the adhesive tape, or any combination thereof.

19. The method of claim 18, wherein that the antiseptic comprises an alcohol.

20. The method of claim 19, wherein the alcohol is isopropyl alcohol.

21. The method of claim 17, further comprising holding the skin taut and pressing the tape firmly on the skin surface while making circular motions on the tape prior to removing the tape from the skin surface.

22. The method of claim 21, wherein that 1-20 circular motions are made on the tape.

23. The method of claim 17, wherein that the tape application is on a skin lesion of the skin surface.

24. The method of claim 23, wherein that the skin lesion:
   is a pigmented skin lesion comprising a mole, dark colored skin spot, or melanin containing skin area; or
   is suspicious for melanoma, lupus, rubeola, acne, hemangioma, psoriasis, eczema, candidiasis, impetigo, shingles, leprosy, Chron's disease, inflammatory dermatoses, bullous diseases, infections, basal cell carcinoma, actinic keratoses, merkel cell carcinoma, sebaceous carcinoma, squamous cell carcinoma, and dermatofibrosarcoma protuberans.

25. The method of claim 23, wherein the skin lesion is from about 5 mm to about 20 mm in diameter.

26. The method of claim 17, wherein the skin surface:
   is not located on the areas selected from the group consisting of palms, soles of feet, and mucous membranes;
   is not ulcerated or bleeding; or
   has not been previously biopsied.

27. The method of claim 17, further comprising
   detecting the presence of a nucleic acid molecule expressed from C6orf218, preferentially expressed antigen in melanoma (PRAME), IL-6, IL-8, IL-17A, IL-17C, IL-17F, IL-17RA, IL-17RC, IL-21, IL-22, IL-23A, IL-24, IL-26, TNF-α, TNF RSF1A, S100A7, S100A9, CCL20, CXCL1, CXCL5, LCN2, DEFB4A, or a combination thereof; or
   detecting the presence of a nucleic acid molecule expressed from C6orf218 in the skin sample.

28. A system for collecting and mailing a skin sample comprising:
   a) at least one adhesive tape from the tri-fold skin sample collector of claim 1; and
   b) an instruction manual.

29. The system of claim 28, wherein the tri-fold skin sample collector comprises an area for labeling patient information.

30. The system of claim 28, further comprising
   a lab requisition form, provided that the lab requisition form is labeled with a unique barcode that is assigned to the patient sample;
   a permanent marker, a resealable plastic bag, a package for shipping, and a prepaid shipping label; or
   a combination thereof.

* * * * *